United States Patent [19]

Harman

[11] Patent Number: Plant 6,828

[45] Date of Patent: Jun. 6, 1989

[54] PEACH TREE

[75] Inventor: James M. Harman, Woolwine, Va.

[73] Assignee: Adams County Nursery, Inc., Aspers, Pa.

[21] Appl. No.: 166,565

[22] Filed: Mar. 10, 1988

[51] Int. Cl.[4] ..... A01H 5/00

[52] U.S. Cl. ..... Plt./43

[58] Field of Search ..... Plt./43

*Primary Examiner*—Robert E. Bagwill

*Attorney, Agent, or Firm*—Frank B. Robb

[57] ABSTRACT

There is disclosed a peach variety which originated as a seedling of Rio Oso Gem, with pollen from an unknown variety, resulting in production of a peach tree producing a late maturing yellow-fleshed, freestone peach that bears large to very large, round, globose, firm fruit having an attractive deep red skin overcolor, with flesh that is golden yellow in color, slow softening with a superior sweet and delicious flavor, the trees being moderately large, vigorous, and regularly productive.

1 Drawing Sheet

GENERAL DESCRIPTION OF THE INVENTION

For purposes of identification and commercial use, my new variety will be known as Harmon.

My new variety of Peach Tree originated as a seedling of Rio Oso Gem, U.S. Plant Pat. No. 84, with pollen from an unknown variety and germinated as a seedling in my orchard near Woolwine, Va.

After this seedling fruited, it was evaluated for several seasons, and these evaluations confirmed that the fruit produced had the outstanding characteristics that I felt were desirable. Scions were cut and grafted on newly planted seedling rootstocks, these grafted trees fruited subsequently and further evaluation confirmed the fruit was large to very large, round, globose, firm, sweet, and attractive. In addition to these trees, bud-grafted trees were also true to type.

These trees of my new variety have exhibited a vigorous spreading growth habit. They are moderately large and regularly productive. Fruit from these trees is as expected very large, round, globose, firm with skin having an attractive deep red color.

The fruit flesh is golden yellow, slow softening, non-melting, with a superior sweet and delicious flavor.

The fruit ripens starting three to four days after Rio Oso Gem, U.S. Plant Pat. No. 84, and Encore, U.S. Plant Pat. No. 4,572.

Asexual reproduction of my new variety has demonstrated that its combination of characteristics comes true to form and is established and transmitted through succeeding generations. The specimens described herein were grown and observed near Woolwine, Va.

The accompanying drawing, shows typical specimens, one being sectioned, of the fruit and foliage as depicted in color as nearly true as is possible to make the same in a color illustration of this character.

The descriptions used herein, are made in reference to the color chart known as Nickerson Color Fan produced by the Munsell Color Company, Baltimore, Md.

DETAILED DESCRIPTION OF MY NEW VARIETY

Dates of first and last pickings: September 5 and September 14 in Woolwine, Va.

Tree: Moderately large size; vigorous; spreading; hardy; productive; regular bearer.

*Trunk.*—Medium; medium smooth to shaggy.

*Branches.*—Medium stocky; medium smooth; brownish gray; glossy. Lenticels — numerous and medium.

*Leaves.*—Acutely pointed; medium thick; smooth. Length — approximately 6.75 inches to 7 inches. Width — approximately 1.20 inches to 1.5 inches. Color — moderate olive green 7.5GY 4/4. Margins — glandular; coarsly serrate. Petiole — medium long; medium thick. Glands — average number 3; alternate; small; reniform; appressed.

Flowers:

*Date of first blossoms.*—April 8.

*Date of last blossoms.*—April 15. Small to medium; non-showy.

*Color.*—Strong; yellowish pink; 7.5R 7/9.

Fruit:

*Maturity when described.*—Eating; firm ripe. Date — Sep. 7, 1987.

*Size.*—Large to very large; axial diameter 3 to 3.16 inches; transverse in suture planes 3.16 to 3.25 inches; at right angles to suture planes 3 to 3.16 inches.

*Form.*—Uniform; unsymmetrical; round globose.

*Suture.*—Shallow; extends from base but discontinues at apex.

*Ventral surface.*—Rounded; lipped moderately toward base; lips unequal.

*Cavity.*—Abrupt; suture showing on one side; depth 0.5 inch; breadth 0.5 inch; no markings.

*Base.*—Rounded.

*Apex.*—Short; pistil point.

*Stem.*—Short length; stout; pubescent.

*Skin.*—Medium thick; free; tendency to break; pubescent. Color — 45 to 65 percent deep red 5R 3/7; 35 to 55 percent speckled bright red om moderate orange yellow 10 YR 7/10. Does not roll up when rubbed.

Flesh:

*Color.*—Golden yellow with red mottled next to stone.

*Surface of pit cavity.*—Red.

*Amygdalin.*—Scant.

*Texture.*—Firm melting.

*Fibres.*—Few tender; slow softening.

*Ripens.*—Fairly even.

*Flavor.*—Superior; sweet.
*Aroma.*—Wanting.
*Eating quality.*—Best.

Stone: Free.
*Fibers.*—Part from flesh smoothly.
*Size.*—Large; length 1.75 inches; thickness 1 inch.
*Form.*—Oval; full apex.
*Base.*—Broad.
*Apex.*—Acuminate.
*Sides.*—Curved on left side; unequal.
*Surface.*—Furrowed near base.
*Ridges.*—Ragged toward base.

Uses: Market; dessert; culinary; canning.

Keeping quality: Medium to good.
Shipping quality: Good.
No particular resistance noticed to disease and insects.

I claim:

1. A new and distinct variety of yellow freestone peach, substantially as illustrated and described, characterized as to novelty by a vigorous growth habit, regular bearing and the ability to yield large to very large, firm, round, globose, deep to bright red color, slow softening fruit, having a superior sweet flavor which commonly ripens three to four days after the Rio Oso Gem and Encore varieties.

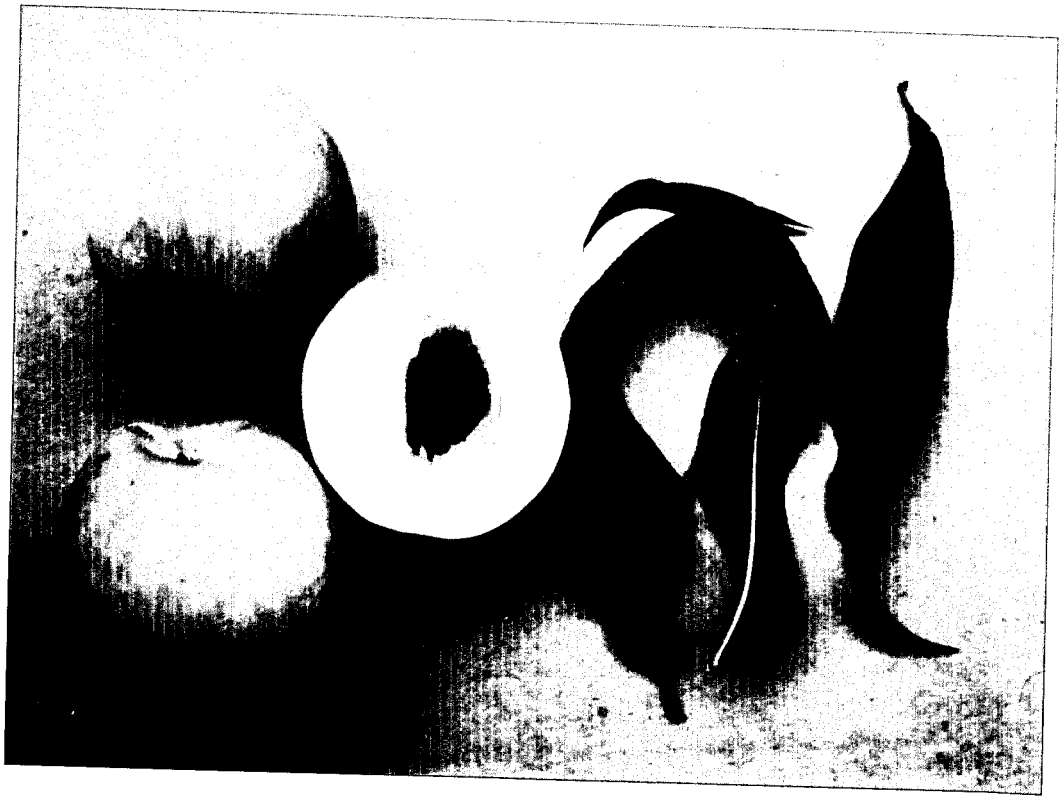

* * * * *